United States Patent [19]
Adell

[11] Patent Number: 5,582,517
[45] Date of Patent: Dec. 10, 1996

[54] MULTI-LAMINAR DENTAL IMPRESSION TRAY ASSEMBLY

[76] Inventor: Loren S. Adell, 200 Adell Blvd., Sunnyvale, Tex. 75182

[21] Appl. No.: 55,144

[22] Filed: Apr. 29, 1993

[51] Int. Cl.⁶ .................. A61C 3/00; A61C 9/00
[52] U.S. Cl. .................. 433/6; 433/214; 433/71
[58] Field of Search .................. 433/37, 48, 71, 433/214; 128/861, 862

[56] References Cited

U.S. PATENT DOCUMENTS

| | | | |
|---|---|---|---|
| 1,234,958 | 7/1917 | Supplee | 433/48 |
| 2,011,860 | 8/1935 | Kalvin | 433/48 |
| 2,053,914 | 9/1936 | Mann | 433/48 |
| 2,183,624 | 12/1939 | Schwartz | 433/71 |
| 2,634,500 | 4/1953 | McAdoo | 433/48 X |
| 2,833,278 | 5/1958 | Ross | 128/862 |
| 3,124,129 | 3/1964 | Grossberg | 128/862 |
| 3,654,703 | 4/1972 | McAdoo . | |
| 4,668,188 | 5/1987 | Wolfenson et al. | 433/37 |
| 5,011,407 | 4/1991 | Pelerin | 433/37 X |
| 5,031,638 | 7/1991 | Castaldi | 128/861 |
| 5,035,613 | 7/1991 | Breads et al. | 433/6 |
| 5,082,007 | 1/1992 | Adell | 128/861 |

*Primary Examiner*—Nicholas D. Lucchesi
*Attorney, Agent, or Firm*—George L. Boller

[57] ABSTRACT

A multi-laminar impression material is supported in a tray to form an impression tray assembly. The impression material comprises two lamina that are bonded together. One lamina is relatively softer than the other. The one lamina faces the arch while the other lamina is disposed against the tray. The impression material may also be bonded to the tray. In a specific preferred embodiment, the tray and both lamina of the impression material are ethylene vinyl acetate.

17 Claims, 2 Drawing Sheets

MULTI-LAMINAR DENTAL IMPRESSION TRAY ASSEMBLY

FIELD OF THE INVENTION

This invention relates generally to dentistry, and in particular to a device for taking an impression of a dental arch that is suitable for making an accurate cast of the arch.

BACKGROUND AND SUMMARY OF THE INVENTION

Certain dental procedures involve taking an impression of a dental arch, using the impression to create a cast of the arch, and using the cast to fabricate an appliance for the arch. In some cases full arch impressions are taken of both arches, in others only one arch is involved, and in still others only partial arch impressions are taken. Common to all of these however is the necessity that the impression material taken an impression that includes the crowns of teeth and at least the adjoining gum margin.

The prevailing clinical practice for taking an impression of a dental arch comprises the use of an outer tray conforming to the shape of the arch that is filled with an impression taking material. This outer tray is typically metal although non-metal trays are known. The impression taking material is typically a clay like composition that is initially soft when placed intra-orally and that hardens around the arch after the arch is impressed into it. This material is alginate, and it is the typical clinical practice for the material to be prepared in the dentist's office and placed in a tray just prior to the taking of a patient's impression. The dentist and staff must devote time to this preparation and often to holding the tray engaged with the patient's arch while the impression taking material sets. Moreover, anyone who has been treated by this procedure is apt to agree that the process is rather unpleasant, and this is due to a large extent to the nature of the impression taking material. A further aspect of using such material is that it takes at least several minutes to set, and once it has set, it cannot be re-softened.

In spite of certain characteristics that are generally considered undesirable, this prevailing clinical practice has continued for quite a few years without significant change. As mentioned above, plastic outer trays are known, and in at least one instance it has been proposed to use such a tray directly for taking an arch impression. U.S. Pat. No. 4,569,342 discloses such a tray, which is also alleged to be suitable for subsequent use by the patient as a dental The tray of that patent is described to be made of methacrylic hexyl ester. Other U.S. Pat. Nos. relating to arch impression devices are: 2,845,708; 3,302,289; and 3,537,179. Other patents that relate to plastic trays used for other purposes such as application of medicinal compositions are: U.S. Pat. Nos. 3,955,281; and 4,173,505.

The present invention relates to a new and unique impression tray assembly for taking an impression of a dental arch including the crowns of teeth and at least the adjoining gum margin, such impression tray assembly being characterized by a multi-laminar impression taking material wherein one lamina has characteristics different from those of another lamina. According to a preferred embodiment of the invention, these two lamina are ethylene vinyl acetate of different durometers and one lamina is injection-molded onto the other. The one lamina that is injection-molded onto the other has a lower durometer than that of the other. This lower durometer lamina is for facing the arch whose impression is to be taken while the higher durometer lamina is for facing an even higher durometer tray that holds the multi-laminar impression taking material. While it may be possible for the multi-laminar impression taking material to simply be placed into the tray, it is believed that a better device is created by having the impression taking material bonded to the tray. Accordingly, a preferred method for fabricating a device according to to principles of the invention is to injection mold the higher durometer lamina of the impression material directly onto the tray, and then injection mold the lower durometer lamina of the impression taking material onto the higher durometer lamina of the impression taking material.

The invention offers important advantages over the prevailing practice. First, the device can be fabricated in a hygienic environment and packaged in a hermetically sealed enclosure. The enclosure is opened only prior to use so that the hygienic integrity of the device is assured, both to the dentist and the patient. The device is prepared for use by heating it to an extent sufficient to render the impression taking material sufficiently soft and formable so that the desired arch impression can be taken. The device is then intra-orally placed onto the arch and held there for an amount of time that will assure that details of the arch impression will not be lost due to deformation or distortion during removal of the device from the arch. This can be a shorter time than is required under the currently prevailing practice.

Another advantage is that the procedure is less unpleasant for the patient. Placement of a warm plastic device onto an arch is believed appreciably less objectionable than placement of a device with a mass of claylike material in a cold and hard metal tray. It is also believed that a patient will be less prone to gagging, and the impression taking material of the invention can, if desired, be provided with an agreeable flavoring, such as mint.

The applicant's development of the invention has revealed that exceptionally fine detail can be obtained in an impression due to the particular materials that are used in the presently preferred embodiment that is described in detail herein, although it is to be understood that principles of the invention are in some respects broader than these particular materials. It is believed that what may be described as a synergistic effect is obtained through the multi-laminar construction of the impression taking material using a relatively low durometer, relatively high vinyl acetate content for the lamina that is to face the arch and a somewhat higher durometer ethylene vinyl acetate for the adjoining lamina onto which the former lamina is injection molded. While the use of ethylene vinyl acetate is not broadly new in intra-oral devices, it is believed that the Applicant is the first to recognize that it can be used in an impression tray for taking an impression of a dental arch that includes the crowns of teeth of the arch and at least the adjoining gum margin. Moreover, it is believed that the use of the multi-laminar construction for the impression taking material and the creation of a multi-laminar assembly which comprises beth the multi-laminar impression taking material and an outer plastic tray are also utterly novel. The use of the particular relatively low durometer, relatively high vinyl acetate content for the lamina that faces the arch is also believed a further utterly novel feature.

The forgoing advantages and features, along with additional ones, will be seen in the ensuing description and claims which are accompanied by drawings. The drawings disclose a presently preferred embodiment of the invention according to the best mode contemplated at this time for carrying out the invention.

DESCRIPTION OF THE PREFERRED EMBODIMENT

Figure 1:
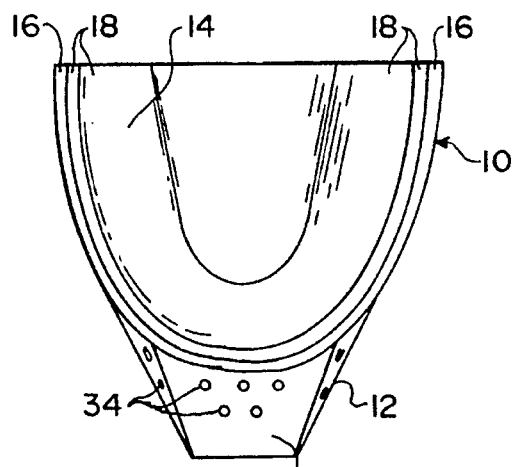
FIG. 1 is a top plan view of a multi-laminar dental impression tray assembly embodying principles of the invention.
Figure 5:
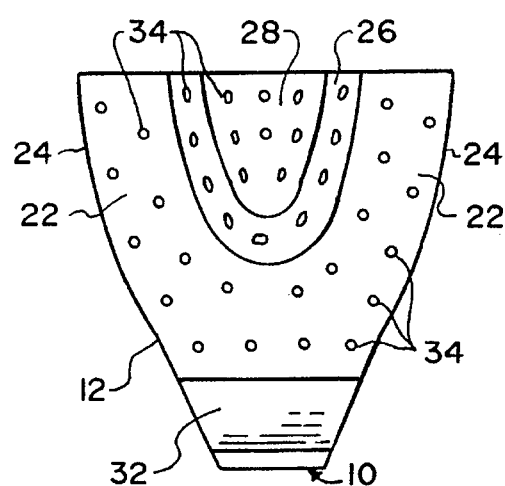
FIG. 5 is a bottom plan view of the assembly of FIG. 1.
Figure 2:
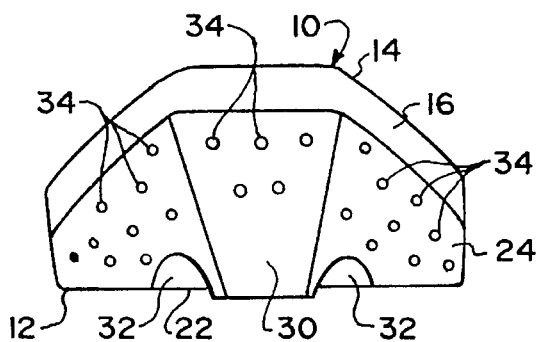
FIG. 2 is a front elevational view of the assembly of FIG. 1.
Figure 4:
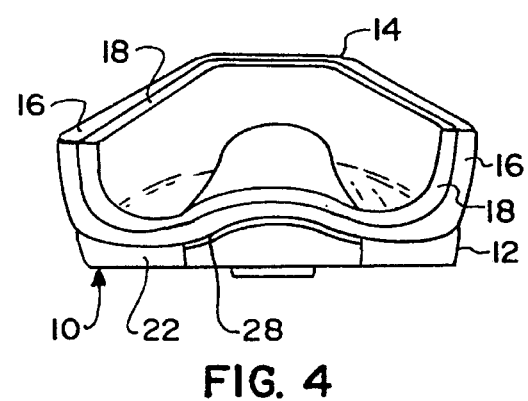
FIG. 4 is a rear elevational view of the assembly of FIG. 1.
Figure 3:
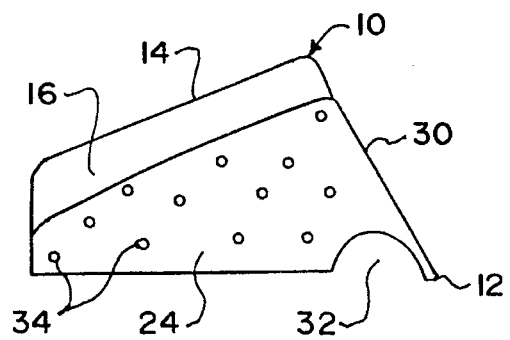
FIG. 3 is a left side elevational view of the assembly of FIG. 1.

FIGS. 1–5 illustrate a multi-laminar dental arch impression tray assembly 10 embodying principles of the invention. Assembly 10 comprises an outer tray 12 that contains multi-laminar impression taking material 14. Impression taking material 14 consists of a first lamina 16 that is disposed against tray 12 and a second lamina 18 that is disposed on lamina 16 opposite tray 12 for facing an arch (not shown) that is to be impressed into the impression taking material. The illustrated embodiment is for taking a full arch impression of an arch, and it is to be understood that principles of the invention may be applied to multi-laminar assemblies that take less than a full arch impression, such as a quadrant for example. A feature of any arch impression taking device that distinguishes it from other intra-oral devices is that when applied to an arch, it extends over the crowns of teeth of the arch and at least the adjoining gum margin. In some cases it may extend over a substantial portion or even the entirety of the gum. One of the important purposes of an arch impression device is that it takes a detailed impression not only of the crowns of teeth, but also of the tooth-gum interface.

Outer tray 12 comprises an occlusal wall 22, a buccal wall 24, and a lingual wall 26 that form a generally U-shaped trough. The bight of the U is closed by a wall 28. The height of buccal wall 24 and that of lingual wall 26 are not uniform throughout; rather each has its greatest height at and immediately adjacent the mesial plane. From there the height of each progressively diminishes in the distal direction. As a result, the top edge of each lies generally in a respective plane that is skewed to the plane occupied by occlusal wall 22. Wall 28 occupies the plane that passes through the top edge of lingual wall 26 and is therefore also skewed in like manner to the plane occupied by occlusal wall 22. At and immediately adjacent the mesial plane, buccal wall 24 is quite planar, having a general trapezoid shape as referenced by the numeral 30. Extending in a direction that is transverse to the mesial plane is a concave slot 32 which is located generally at the junction of the bottom of the trapezoidal shaped portion 30 of buccal wall 24 and occlusal wall 22. This slot provides a locator, or finger rest, that may be helpful to the dentist when he or she places tray assembly 10 intra-orally in a patient. All walls of tray 12 comprise a number of spaced apart perforations except in the vicinity of slot 32. These perforations are designated by the reference numeral 34, and are small circular holes that are about 3/32 of an inch in diameter. The purpose of these perforations is to provide for reception of impression taking material 12. Some impression material may enter the perforations during the process of fabricating the tray assembly, as will be explained in more detail later on, and they provide a means via which some of the impression taking material may be extruded out of the trough during the taking of an impression. While the size, shape, and number of perforations is not critical, they are preferably of such size, shape, number, and location that they do not significantly impair the structural integrity of tray 12.

Tray 12 is preferably a polymer that is injection molded to the described shape. While certain principles of the invention do not depend on the material of tray 12, or on the fabrication of the tray by injection molding, the creation of a tray by injection molding ethylene vinyl acetate to the desired shape provides a certain synergism with a particular impression taking material that is to be described in detail later on. That particular impression taking material is also ethylene vinyl acetate.

Tray 12 provides a reasonably stable subjacent support of impression taking material 14 before, during, and after the taking of an impression of a dental arch. Accordingly tray 12 is a material that has a higher durometer than that of impression taking material 14. In a specific example of tray 12 that is disclosed herein, the material is ethylene vinyl acetate that has a durometer in the range from about 97 to about 90. The wall thickness is generally uniform throughout and may range from about 0.060 inch to about 0.090 inch. It should be appreciated however that in any given tray there can be noticeable thickness differences from place to place, and any one tray may have a different average thickness from that of another tray. Likewise there may be some trays that depart from the aforementioned durometer range, but the purpose of the tray always remains the same, namely to provide reasonably stable support for the impression taking material.

Figure 6:
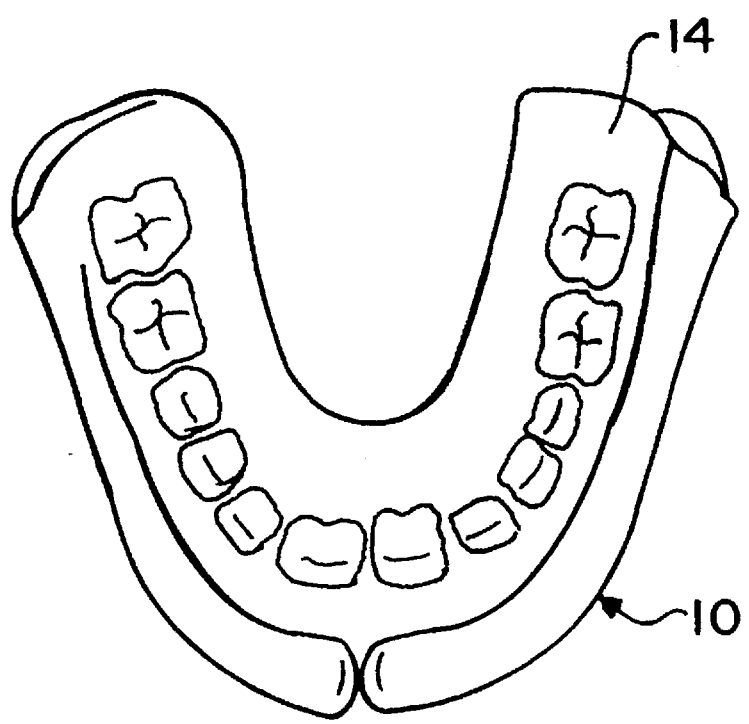
FIG. 6 is a top plan view of the assembly of FIG. 1 after it has been used to take an impression of a dental arch.

An essential attribute of the preferred impression taking material 14 is that it is multi-laminar, specifically consisting of two lamina 16, 18. The preferred material 14 is ethylene vinyl acetate throughout, but the two lamina 16, 18 differ in durometer. In a preferred embodiment, lamina 16 is a relatively higher durometer ethylene vinyl acetate and lamina 18 a relatively lower durometer ethylene vinyl acetate. Specifically, lamina 16 has a durometer of substantially about 73 while lamina 18 has a durometer that is no greater than substantially about 34. Lamina 16 has a vinyl acetate content of substantially about 33% by weight while lamina 18 has a vinyl acetate content of substantially about 46% by weight. The combination of these two lamina to create an arch impression taking material has been found to produce a synergism whereby an arch impression can be taken relatively efficiently, relatively comfortably, and relatively free of messiness with a result that possesses detail enabling a sufficiently detailed cast of the arch to be fabricated by conventional cast fabrication techniques. FIG. 6 is an attempt to portray the detail, but the extent to which the detail can be obtained can only be fully appreciated by seeing an actual device and the cast made from it.

One of the reasons why such great detail can be obtained is believed due to the properties of lamina 18. In order to prepare impression taking material 14 to take an impression, assembly 10 is heated to soften the impression taking material. When sufficiently softened, lamina 16 is capable of taking a impression. Lamina 18 is even more formable, having almost a certain fluidity. This allows lamina 18 to flow into small spaces. The result is that lamina 16 takes the general impression while lamina 18 picks up the detail. Since lamina 18 remains in covering relation to lamina 16, full detail is obtained throughout the entire impression.

Consequently, a detailed dental arch cast can be made from the impression.

During the taking of an impression, assembly 10 is forced against the arch that is being impressed into its impression material. The impression material is displaced within the tray and where lamina 16 overlies a perforation 34, some material may be extruded through the perforation. Since the greatest pressure will likely be exerted on the occlusal plane, some of the material of lamina 16 will be extruded through the perforations in occlusal wall 22, and to a lesser extent in the lingual and buccal walls 26, 24. Such extrusions however create nothing more than tiny buttons of material that remain integrally joined with lamina 16.

A typical preparation of assembly 10 for taking an arch impression comprises placing it in water having a temperature of about 168° F.–170° F. for an amount of time sufficient to soften impression taking material 14. A typical amount of time is about two minutes to about two minutes and fifteen seconds. After sufficient softening of the impression taking material so that a detailed impression can be taken, assembly 10 is applied to the arch. It is held there for an amount of time sufficient to assure that the impression material will take the detail of the arch and then have sufficient stability not to lose that detail when the assembly is removed. Typical holding times are on the order of a minute or two.

It should be understood that in any device embodying principles of the invention, there may be some variation in processing due to particular circumstances and/or specific details of the construction of the device. The exemplary times just mentioned are for a particular device having particular thicknesses for the lamina. On average, such thicknesses are about 0.100 inch each for each lamina 16 and 18. Over the extent of any given device, there may be some variation in thickness of an individual lamina or laminas. Likewise, there are also certain minimum thicknesses that must be observed. For example, tray 12 must have sufficient thickness to provide adequate support for the impression material and to prevent distortion. Lamina 16 and 18 must also have certain minimum thicknesses in order to take an impression that will extend at least over the gum margin. Excessive thicknesses should however also be avoided since it has been observed that when impression material lamina are too thick, there may be some distortion. Excessive heating can also introduce distortion.

While the materials that have been specified above are definitely preferred, a satisfactory device may be fabricated using different materials. For example, a device which for its lamina 16 uses ethylene vinyl acetate having a durometer of substantially about 40 and a vinyl acetate content of about 40% by weight can be satisfactory. It is also believed that the above specified lamina 18 can be satisfactorily used with other lamina 16 other than ethylene vinyl acetate.

In order for the impression material to perform, it is important that the lamina be properly bonded. A preferred form of bonding is by injection molding one lamina onto the other. For example, lamina 18 can be injection molded onto lamina directly without the use of separate intervening adhesive. This type of bonding can be performed when both lamina are ethylene vinyl acetate, and very satisfactory bonding results. It is also preferred that the impression material too be bonded to tray 12. Accordingly, a preferred method for fabricating an assembly 10 comprises injection molding tray 12 in a mold cavity having upper and lower halves. When the cavity is opened after molding, tray 12 remains in the lower half. That lower half is then associated with a different upper mold half that comprises a cavity for molding lamina 16, and lamina 16 is then fabricated by injection molding material into the cavity space of the closed halves so that lamina 16 is directly bonded onto tray 12. The upper mold half is then removed and replaced by a further upper mold half that comprises a cavity for molding of lamina 18. Lamina 18 is then injection molded in that cavity and directly bonds to lamina 16. This process of creating assembly 10 is sometimes referred to as pyramid molding.

During the molding of lamina 16 onto tray 12, some of the injected material may flow into perforations 34. This also provides a mechanical interlocking. In certain embodiments of the invention, mechanical interlocking may be sufficient to join the impression material; with the tray; in other words, the impression material doesn't have to be bonded to the tray. However, the preferred procedure described above does contemplate bonding of the impression material to the tray by injection molding, and in that case, a preferred material for the tray is also ethylene vinyl acetate, but of a durometer that is higher than that of lamina 16. For example an ethylene vinyl acetate tray can be fabricated by injection molding material that has a durometer in the range from about substantially 90 durometer to about substantially about 97 durometer. Such a tray should have a thickness of about 0.060 inch minimum at its occlusal wall. Minimum thicknesses for lamina 16 and lamina 18 are about 0.035 inch and 0.045 inch.

Because of differences in size of arch from person to person, assemblies 10 embodying principles of the invention will also be expected to vary in size. For commercial purposes, several different sizes may be manufactured and reasonably cover the range of arch sizes found in the general population.

The example that has been described with reference to FIGS. 1–6 is intended for use in taking an impression of the upper arch. Assemblies embodying principles of the invention may be designed for use in taking impressions of the lower arch. Thus, there will be some differences in shape depending on which arch an impression is to be taken of. Principles of the invention however will remain the same insofar as the multi-laminar nature of the assemblies are concerned. In an assembly for taking an impression of a lower arch, wall 28 will be omitted to provide for the tongue.

While the use of low durometer ethylene vinyl acetate for lamina 18 is one of the principles of the invention, an impression tray assembly that employs a durometer slightly greater than 34 for lamina 18 can produce a device that may be deemed acceptable for some uses. An example would be one in which lamina 18 is substantially 40 durometer ethylene vinyl acetate containing about 40% vinyl acetate by weight, and lamina 16 is ethylene vinyl acetate having substantially about 73 durometer and 33% vinyl acetate by weight. The references that have been herein made to durometer are with respect to the Shore A scale, as is typical for specifying the durometer of ethylene vinyl acetate.

While a presently preferred embodiment of the invention has been illustrated and described, it should be appreciated that principles are applicable to other embodiments. In the claims that follow, it is to be understood that reference to a dental arch is generic to a full and a partial arch and to an upper arch and a lower arch.

What is claimed is:

1. A multi-laminar dental impression tray assembly for taking an impression of a dental arch that is suitable for making an accurate cast of the arch, said tray assembly comprising an outer tray of polymeric material that is shaped to conform to the shape of a dental arch holding arch impression material for taking an impression of a dental arch that includes the crowns of teeth of the arch and at least the adjoining gum margin, wherein said arch impression material comprises a first lamina of polymeric material that is disposed against and bonded to said outer tray and a second lamina of polymeric material of durometer different from that of the polymeric material of said first lamina that is disposed on and bonded to said first lamina opposite said tray for facing an arch that is to be impressed into said arch impression material such that said outer tray and said first and second lamina form a unitary impression tray assembly prior to taking an impression of a dental arch, wherein said second lamina has a lower durometer than that of said first lamina, and wherein said first lamina has a lower durometer than that of said outer tray.

2. A multi-laminar dental impression tray assembly as set forth in claim 1 wherein said outer tray comprises perforations extending through wall portions thereof to allow some of said arch impression material to be extruded through said perforations during the taking of said impression.

3. A multi-laminar dental impression tray assembly as set forth in claim 1 wherein said outer tray, said first lamina, and said second lamina are all ethylene vinyl acetate.

4. A multi-laminar dental impression tray assembly as set forth in claim 3 wherein the durometer of said second lamina is no greater than about 34.

5. A multi-laminar dental impression tray assembly as set forth in claim 4 wherein the durometer of said first lamina is substantially about 73.

6. Arch impression material for disposition in an outer tray to take an impression of a dental arch that includes the crowns of teeth of the arch and at least the adjoining gum margin, said impression material comprising a first lamina of ethylene vinyl acetate that is adapted to be disposed against such an outer tray and a second lamina of ethylene vinyl acetate of durometer lower than that of the ethylene vinyl acetate of said first lamina that is disposed on said first lamina for facing an arch that is to be impressed into said material, wherein the durometer of said second lamina is no greater than about 34.

7. Arch impression material as set forth in claim 6 wherein the durometer of said first lamina is substantially about 73.

8. A multi-laminar dental impression tray assembly for taking an impression of a dental arch that is suitable for making an accurate cast of the arch comprising an outer tray that is shaped to conform to the shape of a dental arch holding arch impression material for taking an impression of a dental arch that includes the crowns of teeth of the arch and at least the adjoining gum margin, wherein said arch impression material comprises first and second lamina that are bonded together by the injection molding of said second lamina onto said first lamina, and wherein said second lamina comprises ethylene vinyl acetate having a durometer no greater than about 34.

9. A multi-laminar dental impression tray assembly as set forth in claim 8 wherein said first lamina comprises ethylene vinyl acetate that has a durometer of substantially about 73.

10. Arch impression material for disposition in an outer tray to take an impression of a dental arch that includes the crowns of teeth of the arch and at least the adjoining gum margin, said impression material comprising first and second lamina that are bonded together by injection molding and wherein one of said lamina comprises ethylene vinyl acetate having a durometer no greater than about 34.

11. Arch impression material as set forth in claim 10 wherein the other of said lamina comprises ethylene vinyl acetate having a durometer greater than the durometer of said one lamina.

12. A multi-laminar dental impression tray assembly for taking an impression of a dental arch that is suitable for making an accurate cast of the arch comprising an outer tray that is shaped to conform to the shape of a dental arch for holding arch impression material for taking an impression of a dental arch that includes the crowns of teeth of the arch and at least the adjoining gum margin, wherein said arch impression material comprises a first lamina of ethylene vinyl acetate that is for facing an arch that is to be impressed into said material and that has a durometer that is no greater than about 34, and at least one additional lamina that is disposed between said first lamina and said outer tray.

13. A multi-laminar dental impression tray assembly for taking an impression of a dental arch as set forth in claim 12 wherein said first lamina is directly injection-molded to said at least one additional lamina without the use of separate intervening adhesive.

14. A multi-laminar dental impression tray assembly for taking an impression of a dental arch as set forth in claim 13 wherein said at least one additional lamina comprises a second lamina that comprises ethylene vinyl acetate that has a durometer greater than that of said first lamina, and said first lamina is directly injection-molded to said second lamina.

15. Arch impression material for disposition in an outer tray to take an impression of a dental arch that includes the crowns of teeth of the arch and at least the adjoining gum margin, said impression material comprising a first lamina of ethylene vinyl acetate that is for facing an arch that is to be impressed into said material and that has a durometer that is no greater than about 34 and at least one additional lamina for facing such an outer tray.

16. Arch impression material as set forth in claim 15 wherein said first lamina is directly injection-molded onto said at least one additional lamina without the use of separate intervening adhesive.

17. Arch impression material as set forth in claim 16 wherein said at least one additional lamina comprises a second lamina that comprises ethylene vinyl acetate that has a durometer greater than that of said first lamina, and said first lamina is directly injection-molded to said second lamina.

* * * * *